United States Patent [19]

Gähwiler et al.

[11] 4,004,576
[45] Jan. 25, 1977

[54] DIRECT INDICATOR DEVICE FOR DETERMINING THE CARDIAC OUTPUT FLOW RATE ACCORDING TO THE THERMODILUTION METHOD

[75] Inventors: Hermann Gähwiler, Zurich; Hansjörg Schlaepfer, Winkel, both of Switzerland

[73] Assignee: Contraves AG, Zurich, Switzerland

[22] Filed: Apr. 28, 1975

[21] Appl. No.: 571,976

[30] Foreign Application Priority Data

May 24, 1974 Switzerland .................... 7100/74

[52] U.S. Cl. .......................... 128/2.05 F; 73/204
[51] Int. Cl.² .......................................... A61B 5/02
[58] Field of Search ...... 128/2 R, 2 A, 2 H, 2.05 R, 128/2.05 A, 2.05 D, 2.05 E, 2.05 F; 73/15 R, 15 B, 194 E, 194 M, 204, DIG. 7; 235/151.34

[56] References Cited
UNITED STATES PATENTS

| 3,446,073 | 5/1969 | Auphan et al. ............... 128/2.05 F |
| 3,678,922 | 7/1972 | Philips .......................... 128/2.05 F |
| 3,777,133 | 12/1973 | Beck et al. ............... 235/151.34 X |
| 3,789,831 | 2/1974 | Kopaniky ....................... 128/2.05 F |
| 3,820,393 | 6/1974 | McGunigle ......................... 73/204 |
| 3,905,229 | 9/1975 | Togio et al. ...................... 73/194 E |
| 3,915,155 | 10/1975 | Jacobson et al. ............. 128/2.05 F |

Primary Examiner—Richard C. Pinkham
Assistant Examiner—Vance Y. Hum
Attorney, Agent, or Firm—Werner W. Kleeman

[57] ABSTRACT

A direct indicator device for determining the cardiac output according to the thermodilution method embodying two temperature sensors connected to the blood circulation for respectively determining the inlet- and dilution temperatures. A clock generator and a scaler connected at the output of the clock generator are provided, the scaler forming a control signal. A respective one of the sensors is connected in circuit with inputs of an associated temperature-pulse frequency converter, the outputs of which are connected with a respective input of a multiplexer. A control input of the multiplexer connected with the output of the scaler serves for the alternate switching-through of a signal from one input and from the other input of the multiplexer to the output thereof in time-dependent function of the control signal. A gate circuit has one input connected with the output of the multiplexer, another input connected with the output of the clock generator and a further input connected with the output of the scaler. The gate circuit has an output at which there appears the clock rate of the clock generator as a function of time on the one hand of the control signal and on the other hand of the signal at the output of the multiplexer, the output of the gate circuit being connected with the input of a counter. The output of the counter is connected with the input of an intermediate storage, and a control input of the counter and a control input of the intermediate storage are connected at the output of the scaler for the summation of the clock repetition rate delivered to the counter and for the storage thereof as a function of time of the control signal. A digital computer has connected therewith a digital indicator device, the computer having inputs connected respectively with the output of the intermediate storage, the output of the clock generator and the output of the scaler.

6 Claims, 5 Drawing Figures

DIRECT INDICATOR DEVICE FOR DETERMINING THE CARDIAC OUTPUT FLOW RATE ACCORDING TO THE THERMODILUTION METHOD

BACKGROUND OF THE INVENTION

The present invention relates to a new and improved construction of a direct indicator device for the determination of the cardiac output flow rate—also known as the cardiac output—according to the thermodilution method wherein there are provided two temperature feelers or sensors connected to the blood circulation for resepectively determining an inlet temperature and dilution temperature of a liquid injected into the blood circulation, the temperature of which deviates from the temperature of the blood.

The principle of the thermodilution method is predicated upon the fact that a certain volume of a liquid is injected into the blood circulation, the temperature of which liquid or injectate deviates from the temperature of the blood. By measuring the course of the temperature of the resultant blood-injectate mixture as a function of time the blood throughflow can be derived according to the well known Stewart-Hamilton formula. For determining the cardiac output or cardiac output flow rate, that is to say, the speed of passage of the blood through the heart there is selected, for instance, as the locality of the injection of the liquid the right atrium (right auricle) and as the locality of the thermodilution measurement the pulmonary artery. There is injected, for instance, 10 ml cold liquid within a few seconds, which for an expected cardiac output of 10 to 20 l/min. constitutes a disturbance which is of no great significance. The pumping function of the heart brings about an intensive degree of commingling or admixing of the blood and the injected liquid. A cold loss at the vessel walls does indeed occur, but since however the temperature gradient does not penetrate too deeply into the surrounding tissues, within the measuring time there is again compensated for the most part the temperature differences owing to the inflowing blood, so that finally no cold is lost. Moreover, inasmuch as the thermal compensation process extends over a number of heart beats (approximately 10) the throughput speed which varies as a function of time can be replaced by an average or mean value, so that there is also reduced the influence of the fluctuations in the temperature of the blood. In particular, the temperature of the blood in the pulmonary artery fluctuates by approximately 0.05° C in rhythm with the breathing, which is to be compared with a temperature change of about 0.3° C caused by the injection of 10 ml of a liquid which is colder by 15° C.

During the construction of a direct indicating device for determining the cardiac output according to the thermodilution method there must be taken into account certain other disturbing influences. Firstly, with changes in position of the patient there oftentimes occur considerable changes in the blood temperature, necessitating the elimination of the measurement result. Then, the recirculation of the blood, i.e. the multiple passage of the same blood particles at the measurement location during the measurement interval necessitates interrupting the measurement after a certain time. Of course—one one of the major advantages of the thermodilution method in contrast to other known methods—resides in the fact that the influence of the recirculation is markedly reduced owing to the action of the body as a thermostat, since with the rather long residence time of the blood in the capillary region there occurs at that location an extensive temperature compensation and, on the other hand, it has been found that the so-called rapid recirculation via the coronary vessels with a normal circulation system does not lead to appreciable distrubances in the measurement. Finally, compensation processes occur between the temperature of the injected liquid and the temperature of the infeed at the catheter. Consequently, the temperature of the injected liquid should be directly determined at its entry into the blood circulation in order to ensure for a faultless or error-free result of the thermodilution measurement.

Catheters are known to the art which possess an arrangement of a liquid infeed and two temperature feelers which are suitable for use with the thermodilution method. As the temperature feelers there are usually employed thermistors or equivalent temperature-sensitive elements. In this way there can be determined at suitable locations of the blood circulation system a respective measurement value designated as the inlet temperature and dilution temperature respectively.

According to a state-of-the-art apparatus for the determination of the cardiac output according to the thermodilution method the thermistor measuring the dilution temperature generates through the agency of a bridge circuit and an amplifier a voltage in the form of a signal which is integrated as a function of time. In this way there can be determined the integral of the dilution temperature curve. With a considerable percentage of the measurements the dilution temperature does not return to the starting value, so that the integration must be interrupted at an empirically determined point in time and the course of the curve must be interpreted by the operator for the purpose of either accepting or rejecting the measurement result. A direct indication, comparison and operation by unskilled laboratory personnel is not possible with such prior art equipment.

According to a further prior art device the evaluation of the measurement result is carried out by a computer. This computer is programmed in such a manner that the point in time of interruption of the integration as well as the acceptance or rejection of the measurement result is determined by the computer itself from the course of the dilution temperature curve. A result is delivered which is to be read-off of a digital voltmeter and which is to be compared with a calibrated value which is separately generated and indicated at the same digital voltmeter. The calibrated value is produced in such a way that with temperature feelers which are connected at the device the measurement values corresponding to the temperature are changed by a predetermined or pre-known amount, thereby simulating pre-known temperature changes. This is brought about, for instance, by applying an additional voltage at the relevant bridge circuit of the thermistor. Thereafter there are manually undertaken at the device the necessary adjustments in order to bring into coincidence the indication with the reference value of a likewise pre-known cardiac output. It should be recognized that notwithstanding the improved indication and comparison nevertheless the equipment cannot be operated by unskilled laboratory personnel.

SUMMARY OF THE INVENTION

With the foregoing in mind, it is a primary object of the present invention to provide a new and improved construction of a direct indicator device for determining the cardiac output flow rate of cardiac output according to the thermodilution method in a manner not associated with the aforementioned shortcomings and drawbacks of the prior art proposals.

Another and more specific object of the invention aims at the provision of an improved construction of device of the previously mentioned character which can be operated in a foolproof manner by even unskilled laboratory personnel and furthermore delivers an extremely exact, reproducible and comparable indication of the cardiac output.

Now in order to implement these and still further objects of the invention, which will become more readily apparent as the description proceeds, the inventive device of the previously mentioned type is manifested by the features that there is provided a clock generator and a scaler connected at the output of the clock generator, the scaler serving to form a control signal. Further, there are provided two temperature-pulse frequency converters having inputs and outputs. A respective temperature sensor or feeler is connected in circuit with the inputs of its associated temperature-pulse frequency converter. The outputs of the converters are connected with a respective input of a multiplexer. The control input of the multiplexer which is connected with the output of the scaler serves for the alternate switching-through of a signal from one input and from the other input of the multiplexer to the output thereof in time-dependent function of the control signal. Additionally, there is provided a gating or gate circuit, having one input connected with the output of the multiplexer, another input connected with the output of the clock generator and a further input connected with the output of the scaler. The gate circuit has an output at which there appears the clock rate of the clock generator as a function of time on the one hand of the control signal and on the other hand of the signal at the output of the multiplexer, the aforementioned output of the gate circuit being electrically connected with the input of a counter. The output of the counter is connected with the input of an intermediate storage, and the control input of the counter and the control input of the intermediate storage are connected at the output of the scaler for the summation of the repetition rate delivered to the counter and for the storage thereof as a function of time of the control signal. There is also provided a digital computer with which there is connected a digital indicator device, the computer having inputs connected respectively with the output of the intermediate storage, the output of the clock generator and the output of the scaler.

There is preferably provided at least at one temperature-pulse frequency converter a control input for changing the pulse frequency corresponding to a temperature, and this control input is connected with an output of the computer.

It is even more advantageous to provide a plurality of control inputs at a temperature-pulse frequency converter, these control inputs being connected with a respective output of the computer for realizing different changes of the pulse frequency by the signals of the computer.

According to a preferred construction of the multiplexer such is designated and constructed in a manner that during each respective half-cycle of the control signal the signals alternately arriving at the one input and at the other input of such multiplexer are switched through to its output.

According to a preferred construction of the gate circuit such is constructed so that within each half-cycle of the control signal and during a predetermined number of cycles or periods of the signal emanating from the multiplexer there is switched-through the cycle or clock rate of the clock generator at its output.

According to an advantageous construction of the intermediate storage such is arranged in the computer as the work storage or store thereof.

A device of the aforementioned type can be economically produced while using conventional electronic circuits. In the catheter there can be employed a random number of temperature sensors or feelers, since the characteristics thereof are introduced into the computer which carries out the required calculations and corrections. Also the functional reliability of the device is continuously monitored and checked by the computer, so that if for instance the catheter is damaged there is delivered a warning which permits interrupting the measurement operation and thus avoids unnecessarily bothering the patient.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE INVENTION

Before considering the invention in greater detail there will initially be briefly considered the principle of the thermodilution method. The present invention is predicated upon the recognition that for the elimination of most of the disturbing effects there is to be determined, on the one hand, the amount of coldness delivered to the blood circulation and, on the other hand, the measurement curve obtained for the dilution temperature, in order to enable proper evaluation, must satisfy criteria. It has been found that from one patient to the other the measurement curves possess certain common characteristics, it being considered to be obvious to derive the criteria from the course of the curves, as will be explained more fully hereinafter in conjunction with FIG. 1.

Figure 1:
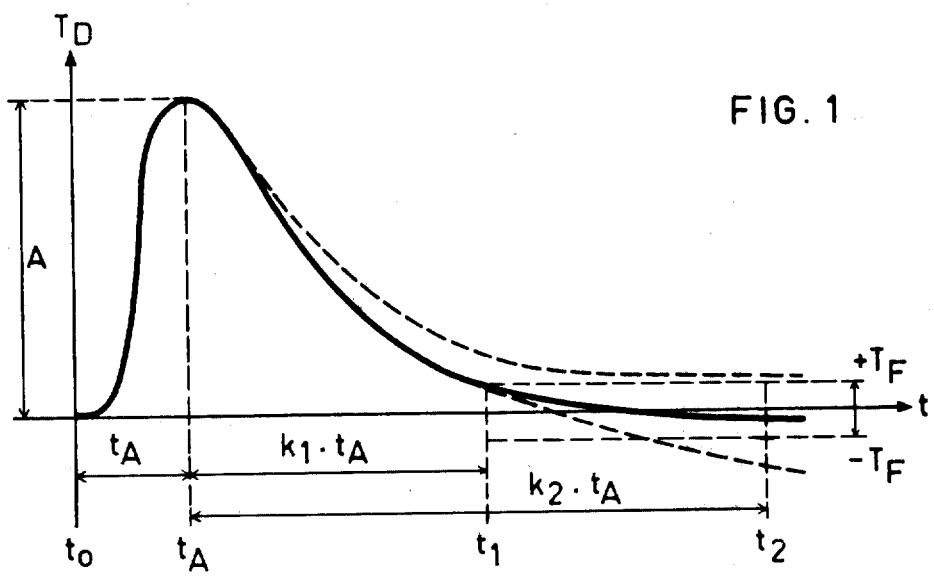
FIG. 1 is a graph of a typical measurement curve as such is obtained at the temperature feeler for the dilution temperature when carrying out the thermodilution method.

In FIG. 1 there is illustrated the course of the dilution temperature $T_D$ as a function of time $t$ after the injection of a cold liquid. Te injection occurs at the point in time $t_o$. The temperature reaches a maximum peak A at the point in time $t_A$. From this data there can be plotted a "window" on the graph which is in the form of a rectangle bounded by the abscissae $t_1$ and $t_2$ as well as by the ordinates $+T_F$ and $-T_F$, wherein with the aid of the constants $k_1$, $k_2$ and $k_3$ which are experimentally determined one time the following calculations are valid:

$t_1 = (1+k_1)t_A$ ; $t_2 = (1+k_2)t_A$ ; $T_F = k_3A$. It has been found that a dilution temperature curve should be located for a certain duration in this window in order to render possible an acceptable measurement of the cardiac output or cardiac output flow rate. In the graphic showing of FIG. 1 the curve shown with full lines constitutes an acceptable curve, whereas the curves shown with broken lines are not acceptable curves.

Figure 2:
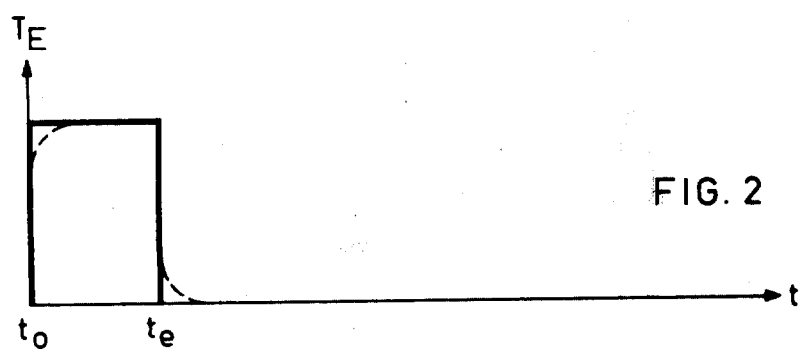
FIG. 2 is a graph which illustrates the inlet temperature-measurement curve simulated during the calibration operation.
Figure 3:
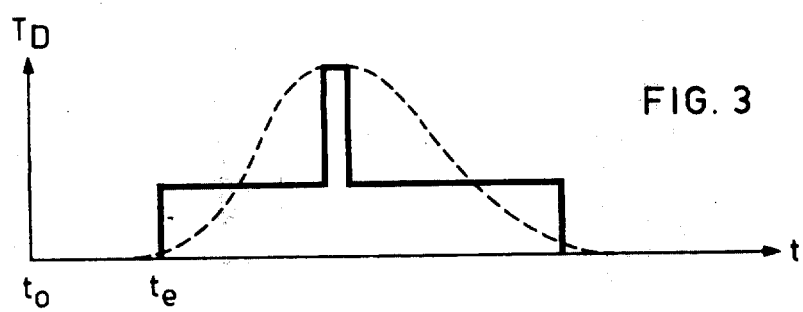
FIG. 3 is a graph which illustrates the dilution temperature-measurement curve simulated during the calibration operation.

Based upon the showing of the graphs of FIGS. 2 and 3 there will be explained the test operation for the monitoring of the functional reliability of the device and for the calibration of the device for the direct indication. There is simulated a patient having a pre-known or predetermined cardiac output which receives an injection of a cold liquid and at whom the inlet temperature as well as the dilution temperature is measured. In FIG. 2 there is shown with a full line the course of the simulated inlet temperature $T_E$ as a function of time $t$; an appropriately effective measurement curve has been approximately illustrated by the broken-line course of the curve. The injection occurs at the point in time $t_o$ and terminates at the point in time $t_e$. In FIG. 3 there is plotted the course of the simulated dilution temperature $T_D$ as a function of the time $t$, the curve being shown with a full line; a corresponding effective measurement curve is approximately shown by the broken-line course of the curve. The rise of the simulated dilution temperature begins at the point in time $t_e$ and its amplitude- and time-course are chosen such that in combination with the simulated inlet temperature there are fulfilled the criteria for a acceptable measurement and the integral of the simulated dilution temperature possesses a predetermined value which is stored and serves as the calibrated value.

Figure 4:
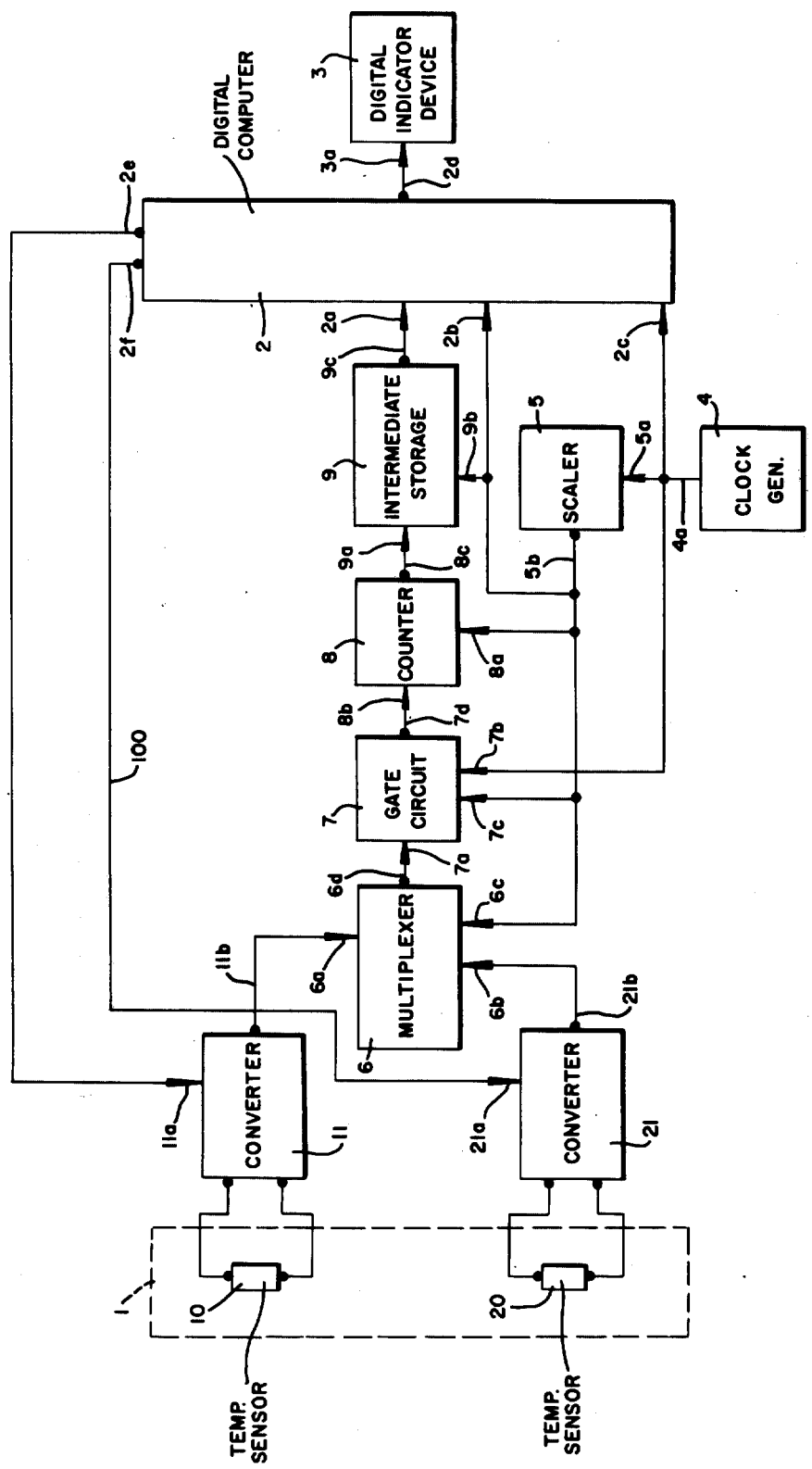
FIG. 4 is a block circuit diagram of an exemplary embodiment of the device of this invention.

Turning attention now to the block circuit diagram of a device constructed according to the teachings of the invention as shown in FIG. 4 it is to be appreciated that the broken-line block 1 symbolizes the catheter. Both of the temperature feelers or sensors 10 and 20 which are located therein are preferably thermistors, although it is to be understood that other temperature-sensitive elements as previously mentioned can be employed. The thermistor 10 measures the inlet temperature and the thermistor 20 the dilution temperature. The thermistor 10 is electrically connected with a temperature-pulse frequency converter 11 and the thermistor 20 is connected with a temperature-pulse frequency converter 21. The converters 11 and 21 preferably contain Wien-bridge oscillators which possess in one of the branches of the bridge the appropriately transformer coupled thermistors. The desired form of the dependency of the cycle duration upon the temperature of the thermistors can be achieved with suitable compensation resistors. There is preferably realized in the converter 11 a linear dependency and in the converter 21 an exponential dependency. The frequency of the oscillators amounts to about 1300 Hz at 25° C. A limiter stage follows the Wien-bridge oscillators in the converters 11, 21. At these converters 11, 21 there are provided the control inputs 11a and 21a respectively, by means of which there can be altered the frequency of the oscillators. These control inputs 11a and 21a of the converters 11 and 21 respectively are supplied with suitable signals for carrying out the test operation from a digital computer 2 which will be considered in greater detail hereinafter, this digital computer 2 having connected therewith a digital indicator device 3. According to a preferred embodiment of the invention the electrical connection between the computer 2 and the converter 21 is constituted by two conductors or lines, so that by suitable activation of the one or the other or both conductors there can be generated a respective predetermined frequency shift, so that in the course of the test operation there can be realized in a very simple manner the curve shape or envelope shown in FIG. 3. Since in the computer 2 there are evaluated relative changes of the cycle duration and not the absolute cycle duration, there is insured that the test operation with the catheter can be carried out both in situ at the blood temperature as well as also at the room temperature. In any event the test operation encompasses the functional reliability of the electrical component or system of the catheter, but for reasons of costs not, however, the temperature-sensitivity of the thermistors.

In totality the device is controlled by the clock rate of a clock generator 4, the output 4a of which is electrically connected with the input 5a of a scaler 5 for forming a control signal. The clock generator 4 preferably generates a 750 KHz-cycle or clock rate and from such there is formed the control signal by scaling down in a ratio of 1:65536 and delivered at the output 5b of the scaler 5.

Figure 5:
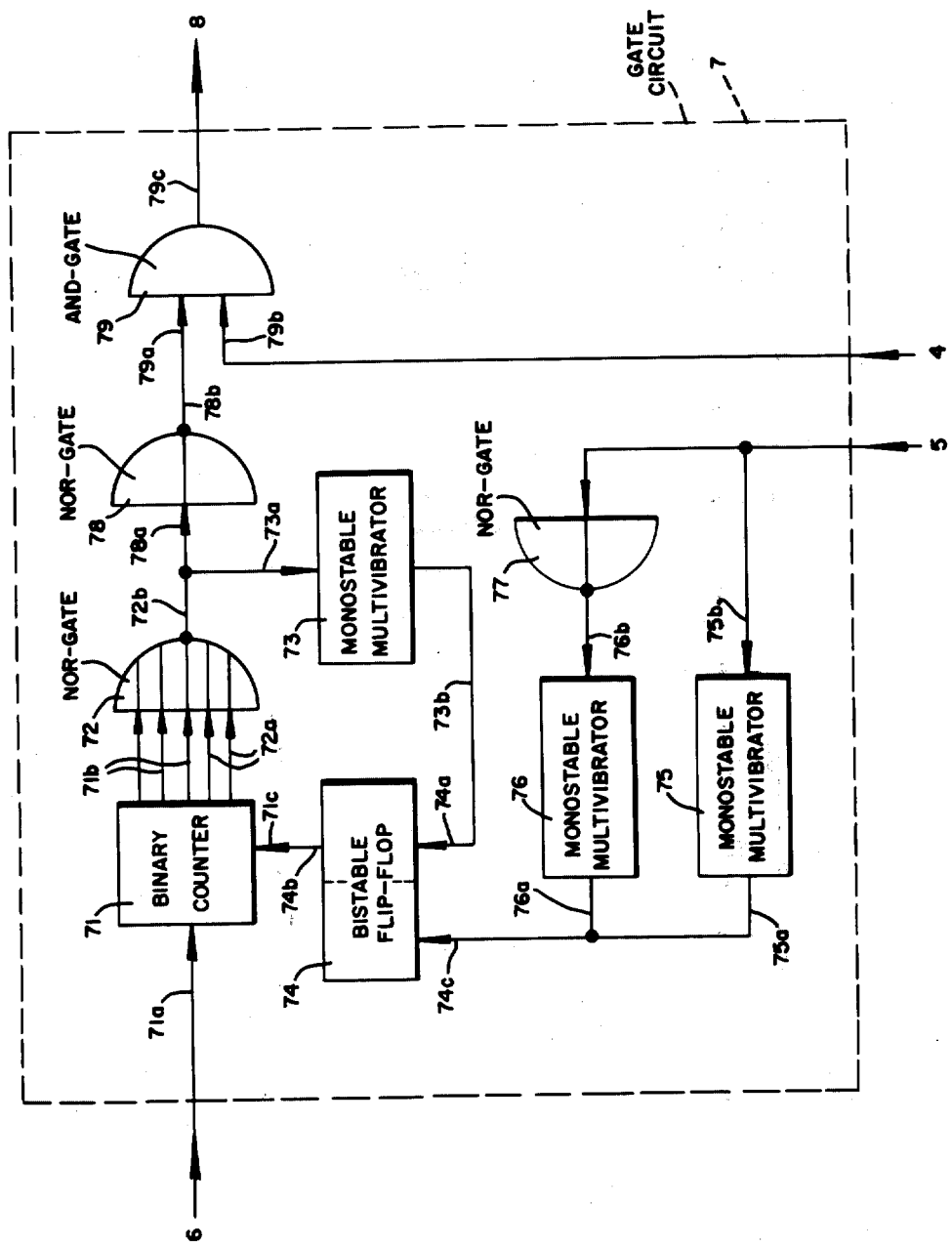
FIG. 5 is a block circuit diagram of a construction of the gate or gating circuit.

The outputs 11b and 21b of the converters 11 and 21 respectively are electrically connected with a respective input 6a and 6b of a multiplexer 6, the control input 6c of which is connected with the scaler 5 so that the multiplexer 6 can be supplied with the control signal appearing at the output 5b of such scaler. The multiplexer 6 functions in the manner of a switch which, during half-cycle of the control signal, alternately switches-through the signals from the converter 11 and from the converter 21 to a gate circuit 7, wherein the output 6d of the multiplexer 6 is connected with the input 7a of such gate or gating circuit 7. A second input 7b of the gate circuit 7 is connected with the output 4a of the clock generator 4 and a third input 7c of the gate circuit 7 is connected with the output 5b of the scaler 5. The gate circuit 7, the details of which will be discussed more fully hereinafter in conjunction with FIG. 5, is constructed so that within each half-cycle of the control signal and during a predetermined number of cycles or periods of the signal from the multiplexer 6 the clock rate of the clock generator 4 is permitted to appear at its output. Preferably the clock rate is switched-through during 31 whole cycles of the multiplex signal. In this way the cycle duration of the pulse frequency from the converters 11 or 21 which is switched-through in each case by the multiplexer 6 is sampled, and specifically as a mean or average value over 31 cycles. With a pulse frequency of approximately 1,400 Hz at 37° C there appear approximately 16,000 pulses per sampling; which for the determination of the inlet temperature at a sensitivity of 0.5%/° C at the thermistor produces a resolution of about 0.012° C, whereas for the dilution temperature with a sensitivity of 0.9%/° C at the thermistor there is realized a resolution of about 0.007° C.

Continuing, an exemplary embodiment of circuitry for the gate or gating circuit 7 has been illustrated in block circuit diagram in FIG. 5. A binary five-place counter 71 receives at its input 71a the output signal of the multiplexer 6. At the five parallel outputs 71b of the counter 71 there appears in binary "modulo 32" numerical system the number of counted cycles or periods of the signal from the multiplexer 6. The outputs 71b of the counter 71 are each connected with a respective input 72a of a NOR-gate 72, so that at the output 72b of the NOR-gate 72 there then appears the logical state "1" when there appears the outputs 71b of the counter 71 the logical state "00000". The logical state appearing at the output 72b of the NOR-gate 72 acts upon the control input 73a of a monostable circuit 73, which delivers at its output 73b a logic 1-pulse when the logic state at the output 72b of the NOR-gate 72 switches from the logic state 0 to the logic state 1. This logic 1-pulse at the output 73b of the monostable circuit 73 acts upon the setting input 74a of a bistable flip-flop circuit 74, the output 74b of which in turn is connected with the resetting input 71c of the counter 71. Consequently, a logic 1-pulse at the output 73b of the monostable circuit or monostable multivibrator 73 is retained as a logic 1-state at the output 74b of the bistable flip-flop circuit 74, with the result that the counter 71 is blocked owing to the logic 1-state appearing at its resetting input 71c and is maintained at the counter state 00000. This always then occurs when the counter state of the counter 71, after counting 31 cycles of the signal emanating from the multiplexer 6, during counting of the next successive cycle reverts back to the logic state 00000. In other words, the counter 71 counts a numerical period modulo 32 and then remains in this logic state 00000.

The resetting input 74c of the bistable flip-flop circuit 74 is connected with a respective output 75a and 76a of two monostable multivibrator circuits or multivibrators 75 and 76. The inputs 75b and 76b of these monostable multivibrators 75 and 76 respectively, have transmitted thereto the control signal emanating from the scaler 5, and specifically in the case of the monostable multivibrator circuit 75 directly, whereas in the case of the monostable multivibrator circuit 76 following an inversion of the control signal in the NOR-gate 77. Hence, during the start of each half-cycle of the control signal there is alternately produced in the one and in the other monostable multivibrator circuit 75 or 76 a logic 1-pulse, which resets the bistable flip-flop circuit 74 to the logic 0-state at its output 74b, whereupon there can be initiated in the counter 71 the counting operation.

From what has been explained above it will be apparent that shortly after the start of each half-cycle of the control signal, as soon as a cycle of the signal emanating from the multiplexer 6 has been counted in the counter 71, the logic state 0 appears and remains at the output 72b of the NOR-gate 72 until there have been counted a complete 31 cycles of the signal emanating from the multiplexer 6, whereupon there again appears the logic state 1 at the output 72b of the NOR-gate 72. The NOR-gate 72 has its output 72b connected with the input 78a of a NOR-gate 78, the output 78b of which is connected with one input 79a of an AND-gate 79. The logic state at the output 72b of the NOR-gate 72, after inversion in the NOR-gate 78, acts at the one input 79a of the AND-gate 79, the other input 79b of which receives the clock rate of the clock generator 4. Consequently, there appears at the output 79c of the AND-gate 79 the cycle or clock rate of the clock generator 4 within each half-cycle of the control signal during the complete 31 cycles of the signal emanating from the multiplexer 6.

The pulse sequences generated in the gate circuit 7 are added or summated in a counter 8 connected at the output 7d of the gate circuit 7. A control input 8a of the counter 8 is connected with the output 5b of the scaler 5. At the start of each half-cycle of the control signal the counter 8 at the null state is in a preparatory start condition, thereafter it counts the number of pulses in the pulse sequence arriving at its input 8b. During the remaining time until the end of the relevant half-cycle of the control signal the counter state appears at the output 8c of the counter 8, thereafter the counter state is extinguished and the process is repeated during the following half-cycle of the control signal. The output 8c of the counter 8 is connected with the input 9a of an intermediate storage 9 which receives the momentary counter state and stores the same during a half-cycle of the control signal. For this purpose a second input 9b of the intermediate storage 9 is electrically connected with the output 5b of the scaler 5. The output 9c of the intermediate storage 9 is electrically connected with the digital computer 2, at which location there are infed to the computer 2 the measurement data which is to be processed. The coaction of the counter 8 and the intermediate storage 9 renders possible, on the one hand, prolonging for a half-cycle of the control signal the duration which is available for the computer for reading-out the momentary or relevant counter state and, on the other hand, the data is coded in the intermediate storage 9 in a manner which can be directly read by the computer 2 and stored in such code. For instance, a 16-bit counter state is broken down into 4 words each having 4-bits in order to be able to read by the computer 4-word-serial-4-bit-parallel. For this purpose the intermediate storage 9 is preferably constructed as a shift register which is contained in the computer 2 as the working storage thereof.

All of the previously mentioned circuits are assembled together from commercially available elements or components and the described logical operations or functions can be realized with such elements generally in different ways by those skilled in the art while still utilizing the basic concepts of the invention. Also the digital indicator device 3 which can be controlled by the computer 2 is a commercially available component and therefore need not be further discussed.

As previously mentioned the digital computer 2 is connected at its one input 2a with the output 9c of the intermediate storage 9. A second input 2b of this digital computer 2 is connected with the output 5b of the scaler 5 and a third input 2c is connected with the output 4a of the clock generator. One output 2d of the computer 2 is connected with the input 3a of the digital indicator device 3, and two other outputs 2e and 2f of such computer 2 are electrically coupled with a respective input 11a and 21a of the temperature-pulse frequency converters 11 and 21, wherein as already mentioned the connection line or conductor 100 leading from the digital computer 2 to the converter 21 preferably consists of two conductors, each of which serves for controlling a respective predetermined frequency shift of the converter 21.

The digital computer 2 can be both an all-purpose computer controlled by program commands as well as also a fixed program special purpose computer. With both variant types of computers there can be obtained the necessary logical operations, so that both types of computers are intended to be embraced by the inventive concepts. The computer is equipped with the requisite circuits in order to be able to obtain from the operator the working commands such as "Start", "Test", "Measurement", "Stop" and also data such as the injected volume of liquid, and on other other hand, in order to be able to indicate the functional conditions such as "Operationally Ready State", "Criteria For Measurement Readiness Fulfilled", "Completion Of Test", "Completion Of Measurement", "Criteria For Measurement Results Not Fulfilled" and so forth.

In order to calculate the cardiac output or cardiac output flow rate there is required the differences of the inlet temperature and the dilution temperature from their values at the rest temperature, i.e. outside of the temperature changes caused by the injection. Since the sensitivity of the temperature feeler or sensor, especially when using thermistors is expressed as a certain relationship, e.g. in %/° C, it is not necessary to know the absolute value of the blood temperature. Upon expiration of the computer program there is taken into account in the computer the pre-known characteristic of the temperature feeler for the temperature differences. Depending upon the permissible expenditure in costs and operation the temperature feeler can be selected in accordance with a predetermined characteristic, or whenever the temperature feeler is exchanged for a new one the characteristic correction provided in the computer program can be accommodated to the new temperature feeler characteristic which is to be determined or pre-known.

The calculation of the cardiac output which is undertaken in accordance with the Stewart-Hamilton formula is carried out on the basis of the data determined by the computer or introduced into the computer according to the following equation:

$$F = \frac{c_i \, g_i \, V_i \, M_E \, K_E}{c_b \, g_b \, J_D \, dt \, K_D} \cdot \frac{60}{1000}$$

wherein the above sysmbols have the following significance:

$c_i$ = Specific heat of the injectate or injected liquid,
$c_b$ = Specific heat of the blood,
$g_i$ = Specific gravity of the injectate,
$g_b$ = Specific gravity of the blood,
$V_i$ = Volume of injectate, possibly simulated,
$M_E$ = Maximum value of the difference between the inlet temperature and its mean or average value, possibly simulated,
$J_D$ = Cumulative value of the difference between the dilution temperature and its means value, possibly simulated,
$dt$ = Duration of a sampling period,
$K_E$ = Slope of the cycle duration/temperature characteristic for the inlet temperature sensor,
$K_D$ = Slope of the cycle duration/temperature characteristic for the dilution temperature sensor.

The factor (60/1000) corresponds to the indication of the cardiac output in 1/min with all data input in cgs-units.

The computer program consists of a pre-program, a measurement program and a test program. While not taking into account the obvious steps such as, for instance, the setting or extinguishing of the indication and the starting conditions, such program is consitituted by the following steps or operations:

Pre-Program: Synchronization with respect to the control signal-half-cycles for differentiating between the inlet temperature and the dilution temperature data, formation of the mean value for the inlet temperature, calculation of the difference of the inlet temperature to its means value, testing the criteria for the constancy of the inlet temperature, formation of the mean value for the dilution temperature, calculation of the difference of the dilution temperature to its means value, testing the criteria for the constancy of the dilution temperature.

Measurement Program: Calculation of the difference of the inlet temperature to its means value, detection of the temperature jump or surge at the inlet temperature, time measurement, detection of the maximum value of the inlet temperature difference, calculation of the difference of the dilution temperature to its mean value, time-integration of the dilution temperature, detection of the maximum value of the dilution temperature difference, calculation of the time-and amplitude boundaries of the window for acceptance of the measurement, testing the number of measurement points in the window as the criteria for the acceptance of the measurement, calculation of the cardiac output.

Test Program: Time measurement, controlling the simulated temperature values, course of the measurement program from the time measurement.

While there is shown a described present preferred embodiments of the invention, it is to be distinctly understood that the invention is not limited thereto, but may be otherwise variously embodied and practiced within the scope of the following claims. Accordingly, What is claimed is:

1. A direct indicator device for the determination of the cardiac output according to the thermodilution method, comprising two temperature sensors adapted to be connected to the blood circulation of a patient for the respective determination of the inlet temperature and the dilution temperature of a liquid injected into the blood circulation of the patient, the temperature of the injected liquid deviating from the blood temperature, a clock generator having an output, a scaler having an input and an output, the output of the clock generator being connected with the input of the scaler for forming a control signal, two temperature-pulse frequency converters, each of said temperature-pulse frequency converters having first input means second input means and an output, one of the temperature sensors being connected with the first input means of one of the converters, the other of the temperature sensors being connected with the first input means of the other converter, a multiplexer having a first input, a second input, a third input and an output, the output of the one converter being connected with the first input of the multiplexer, the output of the other converter being connected with the second input of the multiplexer, the third input of the multiplexer constituting a control input being connected with the output of the scaler for the alternate switching-through of a signal from the first input and the second input of the multiplexer to the output of such multiplexer as a function of time of the control signal, a gate circuit having a first input, a second input and a third input, the first input of the gate circuit being connected with the output of the multiplexer, the second input of the gate circuit being connected with the output of the clock generator, and the third input of the gate circuit being connected with the output of the scaler, the gate circuit having an output at which appears the clock rate of the clock generator as a function of time of the control signal and the signal at the output of the multiplexer, a counter having a first input, a second input and an output, the first input of the counter being connected with the output of the gate circuit, an intermediate storage having a first input, a second input and an output, the output of the counter being connected with the first input of the intermediate storage, the second input of the counter and the second input of the intermediate storage each defining a respective control input and being connected with the output of the scaler for the summation of the clock repetition rate delivered to the counter and for the storage thereof as a function of time of the control signal, a digital computer having a first input, a second input and a third input and at least one output, a digital indicator device having an input connected with the output of the digital computer, the first input of the digital computer being connected with the output of the intermediate storage, the second input of the digital computer being connected with the output of the clock generator and the third input of the digital computer being connected with the output of the scaler.

2. The device as defined in claim 1, wherein said digital computer has a further output, at least one of the temperature-pulse frequency converters having a control input defined by said second input for changing the pulse frequency corresponding to a temperature, said control input of the converter being connected with the further output of the computer.

3. The device as defined in claim 2, wherein at one of the temperature-pulse frequency converters there are provided a plurality of control inputs which are connected with a respective output of the digital computer for attaining different changes of the pulse frequency by means of the signals of the digital computer.

4. The device as defined in claim 1, wherein the multiplexer is constructed such that during each half-cycle of the control signal it alternately switches-through the signals appearing at its first and second inputs to its output.

5. The device as defined in claim 1, wherein the gate circuit comprises circuit means wherein within each half-cycle of the control signal and during a predetermined number of cycles of the signal emanating from the multiplexer it switches-through the clock rate of the clock generator to its output.

6. The device as defined in claim 1, wherein the intermediate storage is arranged in the computer as a work storage.

* * * * *